(12) United States Patent
Bilal et al.

(10) Patent No.: US 9,582,760 B2
(45) Date of Patent: Feb. 28, 2017

(54) EVALUATION OF PREDICTIONS IN THE ABSENCE OF A KNOWN GROUND TRUTH

(71) Applicant: International Business Machines Corporation, Armonk, NY (US)

(72) Inventors: Erhan Bilal, Astoria, NY (US); Gustavo Stolovitzky, Riverdale, NY (US)

(73) Assignee: International Business Machines Corporation, Armonk, NY (US)

( * ) Notice: Subject to any disclaimer, the term of this patent is extended or adjusted under 35 U.S.C. 154(b) by 636 days.

(21) Appl. No.: 14/030,575

(22) Filed: Sep. 18, 2013

(65) Prior Publication Data

US 2014/0279791 A1    Sep. 18, 2014

Related U.S. Application Data

(63) Continuation of application No. 13/827,776, filed on Mar. 14, 2013, now Pat. No. 9,235,808.

(51) Int. Cl.
*G06N 5/02* (2006.01)
*G06F 19/00* (2011.01)
(Continued)

(52) U.S. Cl.
CPC .......... *G06N 5/022* (2013.01); *G05B 13/048* (2013.01); *G06F 19/34* (2013.01); *G06N 5/043* (2013.01)

(58) Field of Classification Search
None
See application file for complete search history.

(56) References Cited

U.S. PATENT DOCUMENTS 6,401,043 B1    6/2002 Stanton, Jr. et al.
7,509,235 B2    3/2009 Bonissone et al.
(Continued)

OTHER PUBLICATIONS

Mitra12, Development of multiple QSAR models for consensus predictions and unified mechanistic interpretations of the free-radical scavenging activities of chromone derivatives [online], Aug. 18, 2011 [retrieved on Feb. 5, 2016]. Retrieved from the Internet:<URL:http://www.google.com/url?sa=t &url=http%3A%2F%Flink.springer.com>.*
(Continued)

*Primary Examiner* — Stanley K Hill
*Assistant Examiner* — Nathan Brown, Jr.
(74) *Attorney, Agent, or Firm* — Fleit Gibbons Gutman Bongini Bianco PL; Jon A. Gibbons (57) ABSTRACT

Disclosed is a novel system, and method to evaluate a prediction of a possibly unknown outcome out of a plurality of predictions of that outcome. The method begins with accessing a particular prediction of an outcome out of a plurality of predictions of that outcome in which the outcome may be unknown. Next, a subsample of the plurality of predictions of the outcome is accessed. The subsample can possibly include the particular prediction. A consensus prediction of the outcome based on the subsample of the plurality of predictions is determined. A proximity of the particular prediction to the consensus prediction is determined. Each prediction is ranked out of the plurality of predictions in an order of a closest in proximity to the consensus prediction to a farthest in proximity to the consensus prediction.

4 Claims, 5 Drawing Sheets

(51) Int. Cl.
*G05B 13/04* (2006.01)
*G06N 5/04* (2006.01)

(56) References Cited

U.S. PATENT DOCUMENTS

| | | | |
|---|---|---|---|
| 7,836,004 | B2 | 11/2010 | Roth et al. |
| 9,009,675 | B2 | 4/2015 | Corthesy et al. |
| 2003/0018512 | A1 | 1/2003 | Dortmans |
| 2003/0050821 | A1 | 3/2003 | Brandt et al. |
| 2004/0187089 | A1 | 9/2004 | Schulz |
| 2005/0055246 | A1 | 3/2005 | Simon |
| 2005/0257136 | A1 | 11/2005 | Charisius et al. |
| 2006/0112388 | A1 | 5/2006 | Taniguchi et al. |
| 2006/0242002 | A1 | 10/2006 | Sun et al. |
| 2007/0050759 | A1 | 3/2007 | Boing et al. |
| 2007/0106541 | A1 | 5/2007 | Raisanen |
| 2007/0156878 | A1 | 7/2007 | Martin et al. |
| 2007/0174342 | A1 | 7/2007 | Maeda et al. |
| 2007/0244840 | A1 | 10/2007 | Carroll |
| 2007/0288520 | A1 | 12/2007 | Hatanaka et al. |
| 2008/0155540 | A1 | 6/2008 | Mock et al. |
| 2008/0249816 | A1 | 10/2008 | Khalilian et al. |
| 2008/0313024 | A1 | 12/2008 | Kunichika et al. |
| 2009/0037569 | A1 | 2/2009 | O'Loughlin et al. |
| 2009/0106059 | A1 | 4/2009 | Megiddo et al. |
| 2009/0204471 | A1 | 8/2009 | Elenbaas et al. |
| 2009/0210282 | A1 | 8/2009 | Elenbaas et al. |
| 2009/0221505 | A1 | 9/2009 | Kolonin et al. |
| 2009/0281830 | A1 | 11/2009 | McNames et al. |
| 2009/0282417 | A1 | 11/2009 | Yoshida |
| 2010/0049568 | A1 | 2/2010 | Louie et al. |
| 2010/0050183 | A1 | 2/2010 | Ogura |
| 2010/0180345 | A1 | 7/2010 | Manchala et al. |
| 2010/0281462 | A1 | 11/2010 | Festa |
| 2010/0304983 | A1 | 12/2010 | Fortmann et al. |
| 2011/0131448 | A1 | 6/2011 | Vasil et al. |
| 2011/0181596 | A1 | 7/2011 | Jacobs |
| 2011/0225565 | A1 | 9/2011 | van Velzen et al. |
| 2011/0231812 | A1 | 9/2011 | Maine et al. |
| 2012/0029978 | A1 | 2/2012 | Olding et al. |
| 2012/0078679 | A1 | 3/2012 | Hodges et al. |
| 2012/0078809 | A1 | 3/2012 | Day |
| 2012/0122701 | A1 | 5/2012 | Ryan et al. |
| 2012/0240187 | A1 | 9/2012 | Childress et al. |
| 2012/0246122 | A1 | 9/2012 | Short et al. |
| 2012/0265573 | A1 | 10/2012 | Van Pelt et al. |
| 2012/0270212 | A1 | 10/2012 | Rabinowitz et al. |
| 2012/0284090 | A1 | 11/2012 | Marins et al. |
| 2012/0284724 | A1 | 11/2012 | Alexander |
| 2012/0296687 | A1 | 11/2012 | Satyanarayana et al. |
| 2012/0331444 | A1 | 12/2012 | Szpak et al. |
| 2013/0029769 | A1 | 1/2013 | Lee |
| 2013/0227285 | A1 | 8/2013 | Bracher et al. |
| 2013/0231969 | A1 | 9/2013 | Van Pelt et al. |
| 2013/0247051 | A1 | 9/2013 | Sun et al. |

OTHER PUBLICATIONS

Courtesy, S. M. et al., "Verification of Complex Research Workflows by Self-Assessment or by Community-Based Assessment," U.S. Appl. No. 13/426,104, filed Mar. 21, 2012.
Meyer, P. et al., "Industrial methodology for process verification in research (IMPROVER): toward systems biology verification," Bioinformatics, Published by Oxford University Press. vol. 28, No. 9, Mar. 14, 2012, pp. 1193-1201. Switzerland.
Conway, K. R. et al., "ClusterMine360: a database of microbial PKS/NRPS biosynthesis," Nucleic Acids Research, University of Ottawa. published online Oct. 26, 2012. Ontario. doi:10.1093/nar/gks993.
Hoen, T. et al., "Deep sequencing-based expression analysis shows major advances in robustness, resolution and inter-lab portability over five microarray platforms," Nucleic Acids Res., vol. 36, No. 21, Sep. 2008. doi:10.1093/nar/gkn705.
Gianola D. et al., "On measures of association among genetic variables," Animal Genetics, vol. 43, Issue Supplement s1, Nov. 2011, pp. 19-35. Wisconsin. Copyright 2012.
Cai G. et al., "Accuracy of RNA-Seq and its dependence on sequencing depth," 8th Annual Biotechnology and Bioinformatics Symposium, vol. 13 (Suppl 13):S5, Oct. 2011. Houston.
Stolovitzky, G., et al., "Verification of Complex Workflows Through Internal Assessment or Community Based Assessment," U.S. Appl. No. 13/426,104, filed Mar. 21, 2012.
Non Final Office Action dated Jun. 18, 2014, received for U.S. Appl. No. 13/426,104.
Non-Final Office Action dated Feb. 3, 2015 received for U.S. Appl. No. 13/827,776.

* cited by examiner

EVALUATION OF PREDICTIONS IN THE ABSENCE OF A KNOWN GROUND TRUTH

CROSS-REFERENCE TO RELATED APPLICATIONS

This application is based upon and claims priority from prior U.S. patent application Ser. No. 13/827,776, filed on Mar. 14, 2013, now U.S. Pat. No. 9,235,808, the entire disclosure of which is herein incorporated by reference in its entirety.

BACKGROUND

The present invention relates generally to verification of complex workflows and, more particularly, to evaluating the quality of a complex workflow, for example those arising in research and development, through the subdivision of the complex workflow into verifiable modules, whose verification is done by internal assessment or by leveraging a community-based assessment.

A complex workflow consists of a number of inputs in the form of (but not limited to) data, signals or material, for example, and a set of processing steps which yield a number of desired outputs in the form of signals, materials or data. These outputs depend both on the inputs and on the processing steps in complex and nontrivial ways. Hence, the goodness or appropriateness of the overall workflow design cannot be assessed using simple or trivial metrics based on the final output. This is so because if the final output is not what is desired, it would be very difficult to understand which step or steps in the complex workflow are at the root of the failure to produce the expected outputs.

Industrial research processes can be described by complex workflows that lead from simple hypotheses to a final product. Workflows are composed of interdependent atomic modules that perform specific research tasks based on the results of other modules.

Stolovitzky et al. proposed a methodology for the verification of such research pipelines that consists of a series of challenges posed at each of the comprising modules. As part of this methodology a trusted third party uses a list of known input-output values to validate the methods used at each research module by comparing the module output to the gold standard. See P. Meyer, J. Hoeng, J. J. Rice, R. Norel, J. Sprengel, K. Stolle, T. Bonk, S. Corthesy, A. Royyuru, M. C. Peitsch, and G. Stolovitzky, "*Industrial methodology for process verification in research (IMPROVER): toward systems biology verification,*" Bioinformatics, vol. 28, no. 9, pp. 1193-1201, May 2012.

Research tasks can often be cast as binary classifiers in such cases like gene network construction, drug sensitivity signatures or therapeutic target discovery. The challenge in this case is to correctly predict the class label of a set of test samples known as the "gold standard." The present invention describes a way to perform this verification task even when a gold standard is not available.

BRIEF SUMMARY

Disclosed is a novel system and method to measure the performance of binary classifiers without the need of a real gold standard. This is achieved by generating a simulated gold standard from the aggregation of all the predictions. At the heart of this is the principle of the "wisdom of crowds," that establishes that under the right conditions, the aggregate of many predictions is a better approximation to the ground truth than any of individual prediction. However, the purpose of this invention is not necessarily to find a good approximation of the ground truth, but to accurately rank the performance of binary classifiers when the ground truth is unavailable.

In one example, a novel system, and method to evaluate a prediction of a possibly unknown outcome out of a plurality of predictions of that outcome is disclosed. The method begins with accessing a particular prediction of an outcome out of a plurality of predictions of that outcome in which the outcome may be unknown. Next, a subsample of the plurality of predictions of the outcome is accessed. The subsample can possibly include the particular prediction. A consensus prediction of the outcome based on the subsample of the plurality of predictions is determined. A proximity of the particular prediction to the consensus prediction is determined. Each prediction is ranked out of the plurality of predictions in an order of a closest in proximity to the consensus prediction to a farthest in proximity to the consensus prediction.

In one example, the consensus prediction is calculated using a plurality of beta distribution and/or normal distributions. The proximity of the particular prediction to the consensus prediction is determined using at least one of predictions, a Jaccard distance, a Hamming distance, an F1 score and a Mathew's correlation coefficient.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as at least one or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. The terms "program", "software application", and the like as used herein, are defined as a sequence of instructions designed for execution on an information processing circuit. A program, computer program, or software application may include a subroutine, a function, a procedure, an object method, an object implementation, an executable application, an applet, a servlet, a source code, an object code, a shared library/dynamic load library and/or other sequence of instructions designed for execution on an information processing circuit. Further, the terms "present application" and "Prediction System" or "application" and "applet" are used interchangeably herein.

The performance of binary classifiers is usually measured against a set of test samples known as the gold standard. Unfortunately, there are many cases for which a gold standard is not available and is hard to generate because of high cost, time constraints or other technical difficulties. The novel contribution of this invention is to establish a set of criterion to measure the performance of binary classifiers without the need of a real gold standard. This is achieved by generating a proxy to the gold standard from the aggregation of all the predictions. At the heart of this is the principle of the "wisdom of crowds," that establishes that under the right conditions, the aggregate of many predictions is a better approximation to the ground truth than any of the individual prediction. However, the purpose of this invention is not necessarily to find a good approximation of the ground truth, but to rank, according to a set of criterion based on a consensus of all the predictions, the performance of binary classifiers when the ground truth is unavailable.

The present application is related to and builds upon the work in co-pending patent application Ser. No. 13/426,104, filed on Mar. 21, 2012, entitled "Verification of Complex Workflows Through Internal Assessment Or community Based Assessment", which is commonly assigned herewith to International Business Machines Corporation, and incorporated by reference in its entirety hereinto.

Overall System

Figure 1:
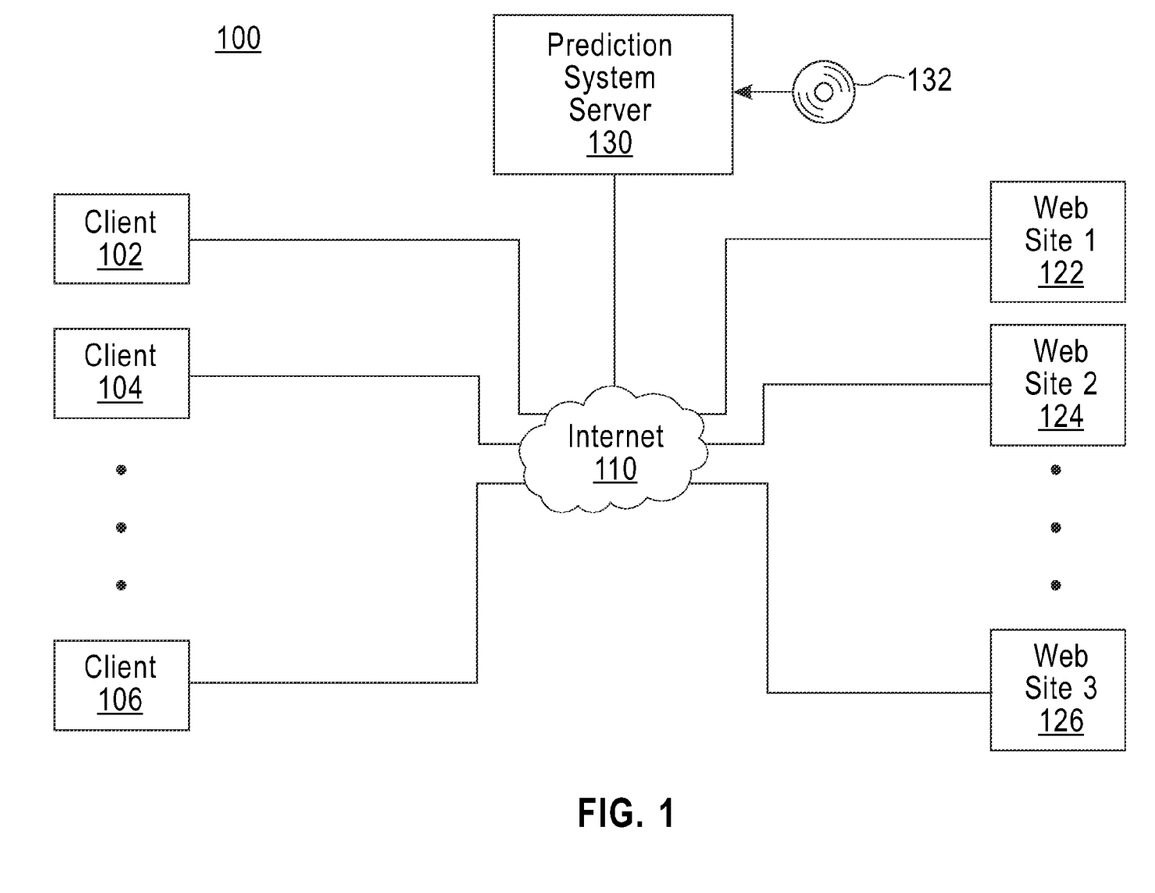
FIG. 1 is a diagram of the overall system for managing evaluation of a prediction of an outcome.

Turning now to FIG. 1 is a diagram of the overall system 100 for managing evaluation of a prediction of an outcome. FIG. 1 shows one or more users or client systems 102, 104, and 106 communicatively coupled over a communications infrastructure 110 to one or more web servers hosting websites 122, 124, and 126. A user system can include a wireless device (e.g., a cellular telephone, a mobile phone, a smartphone and other wireless communication devices such as tablet computers), a laptop/computer, a desktop computer, and other information processing systems.

Prediction system server(s) 130 is also communicately coupled to the communications infrastructure 110. The Prediction system server(s) 130 can be realized in a centralized fashion in one computer system or in a distributed fashion where different elements are spread across several interconnected computer systems. Any kind of computer system—or other apparatus adapted for carrying out the methods described herein—is suitable. A typical combination of hardware and software could be a general purpose computer system with a computer program that, when being loaded and executed, controls the computer system such that it carries out the methods described herein.

In general, the routines executed to implement the embodiments of the present invention, whether implemented as part of an operating system or a specific application, component, program, module, object or sequence of instructions may be referred to herein as a "program." The computer program typically is comprised of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature. Although the exemplary embodiments of the present invention are described in the context of a fully functional computer system, those skilled in the art will appreciate that embodiments are capable of being distributed as a program product via CD or DVD, e.g. CD 132, or other form of recordable media, or via any type of electronic transmission mechanism.

Consensus Scoring

Figure 2:
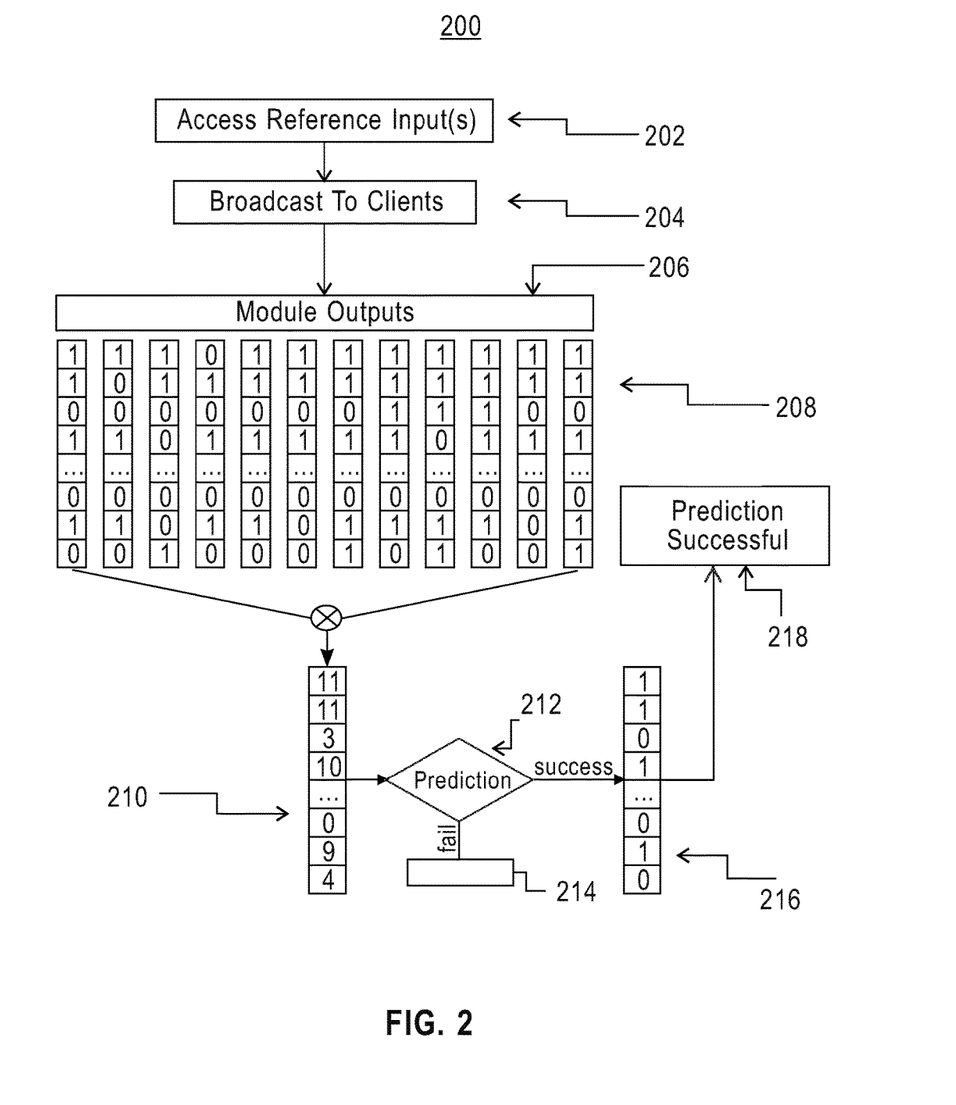
FIG. 2 is a flowchart illustrating running a challenge to determine a consensus prediction.

FIG. 2 is a flowchart illustrating a method 200 of running a challenge to manage a prediction of an outcome from a plurality of predictions of that outcome. It is important to note that the outcome may be unknown in this example. The process begins in step 200 with a reference input 202 being broadcast from the prediction system server(s) 130 or any of the websites 122-126 to one or more client systems 102, 104, 106 through internet 110.

Each participant using the client systems 102, 104, 106 will produce at least one module output 206 in response to accessing the reference inputs 202. The group of vertical vectors 208 represents outputs from the client systems 102, 104, 106. Each vector 208 is a prediction. A prediction corresponds to a plurality of items being predicted, each item represented in one row of the vector 208. For example, each row can be a patient in a cohort of patients who may or may not have a given disease, and the row contains a "1" if the prediction for the item being predicted is that that patient has the given disease and a "0" if the prediction for the item being predicted is that the patient does not have the given disease. The outputs are summed or grouped together in a histogram according to the number of positive results received in vector 210. This is further described in reference to FIG. 3 below.

A consensus prediction is determined in step 212 fitting a mixture model of two unimodal distributions, for example the beta-binomial mixture in Equation 6 below, to the distribution resulting from the aggregate of all the solutions. This distribution fit is compared to the fit by a single unimodal distribution, e.g., the beta-binomial distribution, using a goodness of fit criterion such as Akaike Information Criterion (AIC) or Bayesian Information Criterion (BIC).

If the consensus prediction is not successful, or the single beta-binomial fit is better than the mixture of two beta-binomial distributions, the process ends in step 214. Otherwise the process for creating a consensus prediction from vector 216 is successful and the process ends in step 218 with the "gold standard" identified.

Prediction System

Assume a binary classification problem where the challenge is to predict the E positive items and the N-E negative items out of a total of N items. The N items are organized in a vector, with each item being a row in the vectors 208 of FIG. 2. For any of the proposed solutions, let $P_T$ be the probability that the method predicts an item to be positive given that that item is positive, $P_F$ the probability of predicting an item to be positive given that the item is negative and M the total number of proposed solutions.

For any positive case, the distribution of the number t of solutions that predict that an item is positive given that it is positive is binomial:

$$p(t|T) = \binom{M}{t} P_T^t (1-P_T)^{M-t}$$

Similarly, the distribution of the solutions that predict an item to be positive given that it is negative is:

$$p(t|F) = \binom{M}{t} P_F^t (1-P_F)^{M-t}$$

N is the total number of items.

E is the number of positive items out of N items.

M is the total number of proposed solutions, with each solution making a call (positive or negative) for each of the N items.

T is the realization that a item is positive (or true) in reality.

F is the realization that an item is negative (or false) in reality.

t is a random variable for the number of proposed solutions that label a particular item positive.

$P_T$ is the probability that the method predicts an item to be positive given that the item is really positive (or true).

$P_T^t$ is the probability of picking t items that the method predicts as positive given that they really are positive. So it's just $P_T$ to the power t.

$P_F$ is the probability that the method predicts an item to be positive given that the item is really negative (or false).

$P_F^t$ is the probability that a method picks t items as positive given that they really are negative. So it's just $P_F$ to the power t.

$$\binom{M}{t}$$

is read "M choose t" also called a binomial coefficient. It measures in how many ways we can choose t samples out of a total of M.

For any positive case, the distribution of number of times a sample is labeled positive given that it really is positive is binomial:

$$p(t|T) = \binom{M}{t} P_T^t (1-P_T)^{M-t} \quad (1)$$

Equation 1 is probability of having t solutions out of M proposed solutions predicting a given item to be positive given that that item is positive.

Similarly, the distribution of the number of times a sample is labeled positive given that it really is negative is:

$$p(t|F) = \binom{M}{t} P_F^t (1-P_F)^{M-t} \quad (2)$$

Equation 2 is probability of having t solutions out of M proposed solutions predicting a given item to be positive given that that item is negative.

Therefore the probability function that a sample is labeled positive t times (regardless of whether it really is positive or negative) is:

$$p(t) = p(t|T)\frac{E}{N} + p(t|F)\frac{N-E}{N} \quad (3)$$

The above model assumes that all proposed solutions have constant probabilities of predicting the true class of a given item, and that each item has the same probability of being correctly classified as all other items, which can at best be an approximation. We can model the case of a variable probability of predicting an item as positive given that the item is positive or negative using beta distributions with parameters $(a_1, b_1)$ and respectively $(a_2, b_2)$ to model $P_T$ and $P_F$. The distributions p(t|T) and p(t|F) become the beta-binomial distributions:

$$p(t|T) = \binom{M}{t}\frac{B(t+a_1, M-t+b_1)}{B(a_1, b_1)} \quad (4)$$

$$p(t|F) = \binom{M}{t}\frac{B(t+a_2, M-t+b_2)}{B(a_2, b_2)} \quad (5)$$

$$p(t) = \quad (6)$$
$$w\binom{M}{t}\frac{B(t+a_1, M-t+b_1)}{B(a_1, b_1)} + (1-w)\binom{M}{t}\frac{B(t+a_2, M-t+b_2)}{B(a_2, b_2)},$$
$$w = \frac{E}{N}$$

Equation 6 describes the expected probability that t solutions predict that the same item is positive. This distribution can be fitted to real data by using, e.g., the Maximum Likelihood algorithm if the number of positive test samples is known a priori or by Expectation Maximization (where mixing weight w is the latent variable) if the number of positive test samples is not known.

Parameterization of Prediction System

Figure 3:
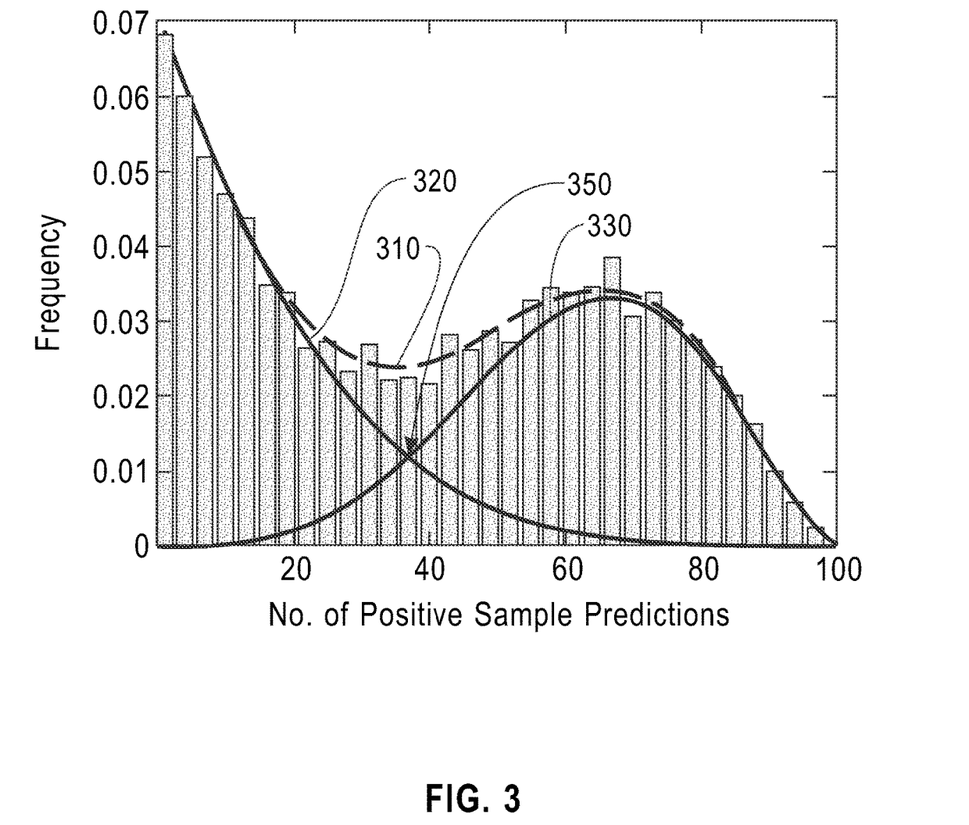
FIG. 3 is an example fit of a mixture of two beta-binomial distributions with scaled components.

FIG. 3 is a histogram graph of an example, and its fit by the mixture of two beta-binomial distributions from Equation 6. The Y axis is a frequency of a given result in vector 210 and the X-axis is the corresponding value in vector 210 whose frequency is plotted on the Y-axis. Curve 310 is a mixture of two beta-binomial distributions. Curves 320 and 330 are the scaled beta-binomial components from Equation 6. Stated differently, this is the step that converts vector 210 into vector 216. The goal is to find the crossing point 350 of curves 320 and 330.

In this case, the research problem is similar to predicting the existence of edges between nodes in a gene network, as described in the DREAM Network Inference Challenges (Marbach D, Prill R, Schaffter T, Mattiussi C, Floreano D, Stolovitzky G, Revealing strengths and weaknesses of methods for gene network inference, Proc Natl Acad Sci USA. April 6; 107(14):6286-91 (2010), and Daniel Marbach, James C. Costello, Robert Küffner, Nicci Vega, Robert J.

Prill, Diogo M. Camacho, Kyle R Allison, the DREAMS Consortium, Manolis Kellis, James J. Collins and Gustavo Stolovitzky, Wisdom of crowds for robust gene network inference, Nat Methods, July 15; 9(8):796-804 (2012)). Proposed solutions by teams are summarized for each pair of genes by adding the number of times it was selected as an edge in the gene network. The resulting solution has the distribution depicted schematically in FIG. 3 and follows the functional form predicted in Equation 6.

Each proposed prediction j can be described as a binary vector 208 in FIG. 2 of dimension equal to the number of items (edges in our example):

$$s_{ij} = \begin{cases} 1, & i \text{ is positive} \\ 0, & i \text{ is negative,} \end{cases} \quad (7)$$
$$j = 1:M$$

Let T be the solution to the equation:

$$f(t) = \qquad (8)$$
$$w\binom{M}{t}\frac{B(t+a_1, M-t+b_1)}{B(a_1, b_1)} - (1-w)\binom{M}{t}\frac{B(t+a_2, M-t+b_2)}{B(a_2, b_2)} = 0$$

This solution is the crossover between the distribution of teams that predicted positive items correctly (true positives) and the teams that predicted negative items as positive (False positives), shown as point 350 in FIG. 3. Then, given the threshold T, the consensus "gold standard", or consensus prediction is:

$$c_i = \begin{cases} 1, & \sum_{j=1}^{M} s_{ij} \geq T \\ 0, & \sum_{j=1}^{M} s_{ij} < T \end{cases} \quad (9)$$

where $c_i$ represent the entries in vector 216 of FIG. 2, and the sums in Equation 9 represent the entries in vector 210 of FIG. 2. In the absence of a real gold standard, the consensus defined in Equation 9 can be used as a proxy for the true gold standard against which all the proposed solutions can be evaluated. FIG. 2 describes a schematic of how the consensus "gold standard" is generated and used to evaluate modules within research pipelines.

The proximity between the prediction j and the consensus gold standard can be any measure of distance between binary vectors, e.g., the Jaccard distance, the Hamming distance, the Mathews correlation coefficient, etc.

Overall Flow of Prediction System

Figure 4:
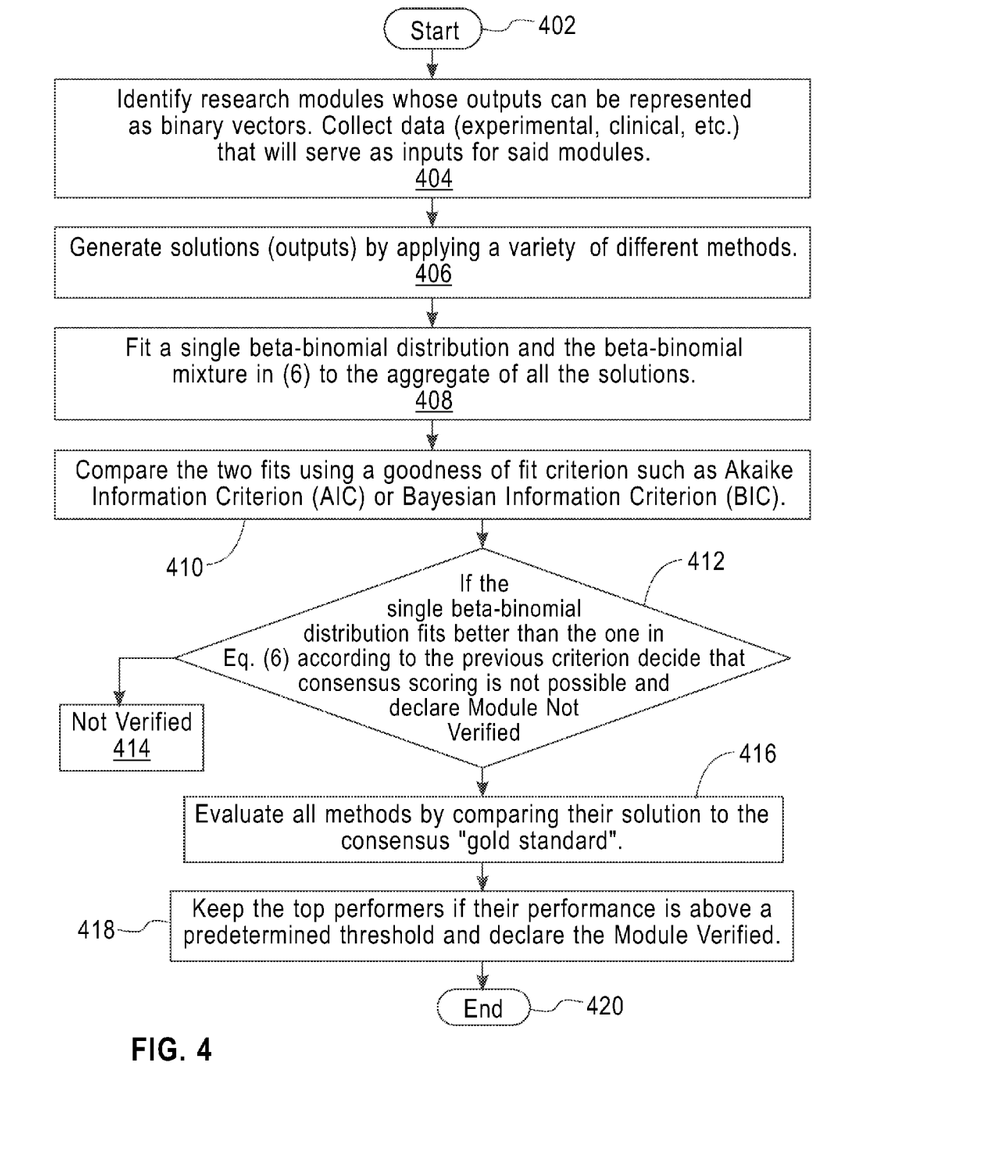
FIG. 4 is a flow chart of an operational phase of carrying out the present invention.

FIG. 4 is a flow chart 400 of an overall flow of prediction system server(s). The process begins in step 402 and immediately proceeds to step 404 in which research modules whose outputs can be represented as predictions are identified and data (experimental, clinical, etc.) is collected that will serve as inputs for said modules. Next in step 406, solutions (outputs) are generated by applying a variety of different methods. In step 408, a single beta-binomial distribution and the beta-binomial mixture in Equation 6 are used to fit the aggregate of all solutions from step 406. The two fits are compared in step 410 using a goodness of fit criterion such as Akaike Information Criterion (AIC) or Bayesian Information Criterion (BIC). A decision block 412 is entered. If the single beta-binomial distribution fits better than the one in Equation 6, then decide that consensus scoring is not possible and declare Module Not Verified in step 414. Otherwise, in step 412, if the single beta-binomial distribution fits worse than the one in Equation 6, then numerically solve Equation 8 and generate the consensus "gold standard" as defined in Equation 9. In step 416, evaluate all methods by comparing their solution to the consensus "gold standard". The top performers are kept in step 418 if their performance is above a predetermined threshold and declare the Module Verified. The process ends in step 420.

Information Processing System

Figure 5:
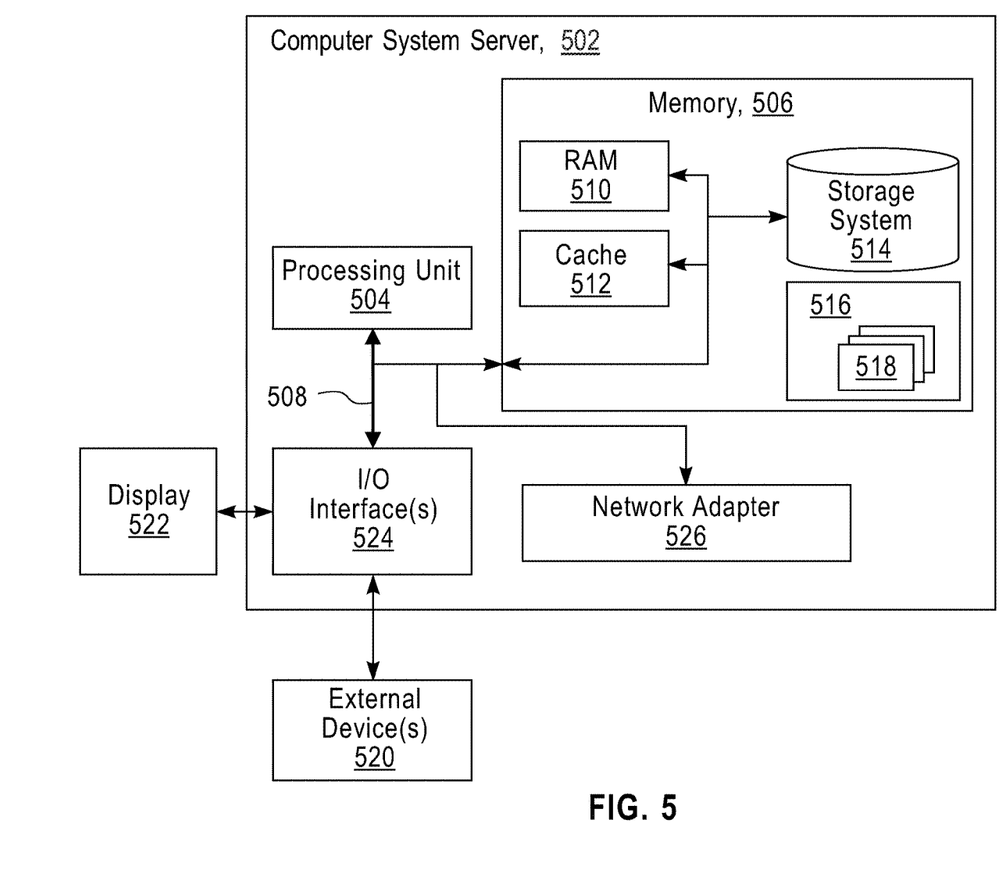
FIG. 5 is a block diagram illustrating a detailed view of an information processing system for carrying out the operation of FIG. 4.

FIG. 5 illustrates one example of a detailed view of an information processing system 502 for carrying out the operation of FIG. 1, which can be deployed in the prediction system server(s) 130. Any suitably configured processing system can be used as the information processing system 502 in embodiments of the present invention. The components of the information processing system 502 can include, but are not limited to, one or more processors or processing units 504, a system memory 506, and a bus 508 that couples various system components including the system memory to the 501 one or more processing units.

The bus 508 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Although not shown in FIG. 5, the main memory 506 includes the prediction system server(s) 110. The system memory 506 can also include computer system readable media in the form of volatile memory, such as random access memory (RAM) 510 and/or cache memory 512. The information processing system 502 can further include other removable/non-removable, volatile/non-volatile computer system storage media. By way of example only, a storage system 514 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 508 by one or more data media interfaces. The memory 506 can include at least one program product having a set of program modules that are configured to carry out the functions of an embodiment of the present invention.

Program/utility 516, having a set of program modules 518, may be stored in memory 506 by way of example, and not limitation, as well as an operating system, one or more application programs (e.g., the prediction system program), other program modules, and program data. Each of the operating system, one or more application programs, other program modules, and program data or some combination thereof, may include an implementation of a networking environment. Program modules 518 generally carry out the functions and/or methodologies of embodiments of the present invention.

The information processing system 502 can also communicate with one or more external devices 520 such as a keyboard, a pointing device, a display 522, etc.; one or more devices that enable a user to interact with the information processing system 502; and/or any devices (e.g., network card, modem, etc.) that enable computer system/server 502 to communicate with one or more other computing devices. Such communication can occur via I/O interfaces 524. Still yet, the information processing system 502 can communicate with one or more networks such as a local area network (LAN), a general wide area network (WAN), and/or a public network (e.g., the Internet) via network adapter 526. As depicted, the network adapter 526 communicates with the other components of information processing system 502 via the bus 508. Other hardware and/or software components can also be used in conjunction with the information processing system 502. Examples include, but are not limited to: microcode, device drivers, redundant processing units, external disk drive arrays, RAID systems, tape drives, and data archival storage systems.

Non-Limiting Examples

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit"," "module", or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable storage product or computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems), and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium or computer readable storage medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A non-transitory computer program product for evaluating a prediction of an outcome out of a plurality of predictions of that outcome, the computer program product comprising instructions configured to perform a method comprising:
   collecting a plurality of clinical data from each patient of a cohort of patients;
   providing a plurality of research modules, each of which having an input for receiving a clinical data of the plurality of clinical data from each patient of the cohort of patients, and each of which having an output for outputting predictions of an outcome that represents a prediction that a patient has a given disease;
   inputting each clinical data of the plurality of clinical data into a respective research module;
   outputting, from the plurality of research modules, a plurality of prediction of outcomes;
   accessing a particular prediction of an outcome out of a plurality of predictions of that outcome in which the outcome may be unknown;
   accessing a subsample of the plurality of predictions of the outcome, with the subsample possibly including the particular prediction;
   determining with a computer, a consensus prediction of the outcome based on the subsample of the plurality of predictions;
   determining a proximity of the particular prediction to the consensus prediction, wherein the consensus prediction is calculated using a mixture of two unimodal probability distributions; and
   ranking each prediction out of the plurality of predictions in an order of a closest in proximity to the consensus prediction to a farthest in proximity to the consensus prediction.

2. A non-transitory computer program product for evaluating a prediction of an outcome out of a plurality of predictions of that outcome, the computer program product comprising instructions configured to perform a method comprising:
   collecting a plurality of clinical data from each patient of a cohort of patients;
   providing a plurality of research modules, each of which having an input for receiving a clinical data of the plurality of clinical data from each patient of the cohort of patients, and each of which having an output for outputting predictions of an outcome that represents a prediction that a patient has a given disease;
   inputting each clinical data of the plurality of clinical data into a respective research module;
   outputting, from the plurality of research modules, a plurality of prediction of outcomes;
   accessing a particular prediction of an outcome out of a plurality of predictions of that outcome in which the outcome may be unknown;
   accessing a subsample of the plurality of predictions of the outcome, with the subsample possibly including the particular prediction;
   determining with a computer, a consensus prediction of the outcome based on the subsample of the plurality of predictions;
   determining a proximity of the particular prediction to the consensus prediction, wherein the consensus prediction is calculated using a mixture of two beta-binomial distributions; and
   ranking each prediction out of the plurality of predictions in an order of a closest in proximity to the consensus prediction to a farthest in proximity to the consensus prediction.

3. A system of for evaluating a prediction of an outcome out of a plurality of predictions of that outcome, the system comprising:
   a memory;
   a processor communicatively coupled to the memory, where the processor is configured to perform
      collecting a plurality of clinical data from each patient of a cohort of patients;
      providing a plurality of research modules, each of which having an input for receiving a clinical data of the plurality of clinical data from each patient of the cohort of patients, and each of which having an output for outputting predictions of an outcome that represents a prediction that a patient has a given disease;
      inputting each clinical data of the plurality of clinical data into a respective research module;
      outputting, from the plurality of research modules, a plurality of prediction of outcomes;
      accessing a particular prediction of an outcome out of a plurality of predictions of that outcome in which the outcome may be unknown;
      accessing a subsample of the plurality of predictions of the outcome, with the subsample possibly including the particular prediction;
      determining a consensus prediction of the outcome based on the subsample of the plurality of predictions, wherein the consensus prediction is calculated using a mixture of two unimodal probability distributions;
      determining a proximity of the particular prediction to the consensus prediction; and
   ranking each prediction out of the plurality of predictions in an order of a closest in proximity to the consensus prediction to a farthest in proximity to the consensus prediction.

4. A system of for evaluating a prediction of an outcome out of a plurality of predictions of that outcome, the system comprising:
   a memory;
   a processor communicatively coupled to the memory, where the processor is configured to perform
      collecting a plurality of clinical data from each patient of a cohort of patients;
      providing a plurality of research modules, each of which having an input for receiving a clinical data of the plurality of clinical data from each patient of the cohort of patients, and each of which having an output for outputting predictions of an outcome that represents a prediction that a patient has a given disease;

inputting each clinical data of the plurality of clinical data into a respective research module;

outputting, from the plurality of research modules, a plurality of prediction of outcomes;

accessing a particular prediction of an outcome out of a plurality of predictions of that outcome in which the outcome may be unknown;

accessing a subsample of the plurality of predictions of the outcome, with the subsample possibly including the particular prediction;

determining, a consensus prediction of the outcome based on the subsample of the plurality of predictions, wherein the consensus prediction is calculated using a mixture of two beta-binomial distributions;

determining a proximity of the particular prediction to the consensus prediction; and ranking each prediction out of the plurality of predictions in an order of a closest in proximity to the consensus prediction to a farthest in proximity to the consensus prediction.

* * * * *